United States Patent [19]

Raines et al.

[11] Patent Number: 4,671,408

[45] Date of Patent: Jun. 9, 1987

[54] TEMPER-RESISTANT PROTECTIVE CAPPING DEVICE FOR FILLED SYRINGES

[75] Inventors: Kenneth Raines; Gary Horner, both of Bethlehem, Pa.

[73] Assignee: Burron Medical Inc., Bethlehem, Pa.

[21] Appl. No.: 746,647

[22] Filed: Jun. 20, 1985

[51] Int. Cl.⁴ .................... B65D 85/72; B65D 45/16
[52] U.S. Cl. .................... 206/365; 206/45.23; 206/1.5; 220/339; 220/324
[58] Field of Search ............ 206/365, 364, 379, 45.23, 206/1.5; 220/339, 324

[56] References Cited

U.S. PATENT DOCUMENTS

| | | | |
|---|---|---|---|
| 1,136,187 | 4/1915 | Waldes | 206/45.23 |
| 1,235,890 | 8/1917 | Gilbert | 206/365 |
| 2,324,436 | 7/1943 | Snyder | 206/45.23 |
| 2,584,721 | 2/1952 | Linneman | 206/379 |
| 2,740,516 | 4/1956 | Renn | 206/365 |
| 3,107,785 | 10/1963 | Roehr | 206/365 |
| 3,612,233 | 10/1971 | Nagpal et al. | 206/387 |
| 3,904,035 | 9/1975 | Metzler et al. | 206/379 |
| 3,913,711 | 10/1975 | Schmid | 206/45.23 |
| 3,930,499 | 1/1976 | Rimbaud | 206/365 |
| 4,098,577 | 7/1978 | Halpern | 206/807 |
| 4,113,104 | 9/1978 | Meyers | 206/807 |
| 4,287,988 | 9/1981 | House | 206/365 |
| 4,300,682 | 11/1981 | Kuchenbecker | 206/470 |
| 4,445,622 | 5/1984 | Sideri | 206/807 |
| 4,558,782 | 12/1985 | Iverson et al. | 206/387 |
| 4,569,442 | 2/1986 | Bushey | 206/470 |
| 4,610,371 | 9/1986 | Karkiewicz | 206/807 |

FOREIGN PATENT DOCUMENTS

| | | | |
|---|---|---|---|
| 242079 | 8/1965 | Austria | 206/379 |
| 987183 | 4/1951 | France | 206/364 |

*Primary Examiner*—Joseph Man-Fu Moy
*Attorney, Agent, or Firm*—Shoemaker and Mattare, Ltd.

[57] ABSTRACT

A tamper-resistant filled syringe protective capping device which comprises a one-piece molded product, comprising a base section having a portion thereof provided with a female luer port, a sterility protector, and two side portions which at their furthest ends are provided with complementary locking structure so that when a filled syringe is inserted into the luer port at the base section of the unit, the two side portions can be folded therearound and locked into position to form a tamper-evident container for maintaining a filled syringe in tamper-proof condition.

6 Claims, 5 Drawing Figures

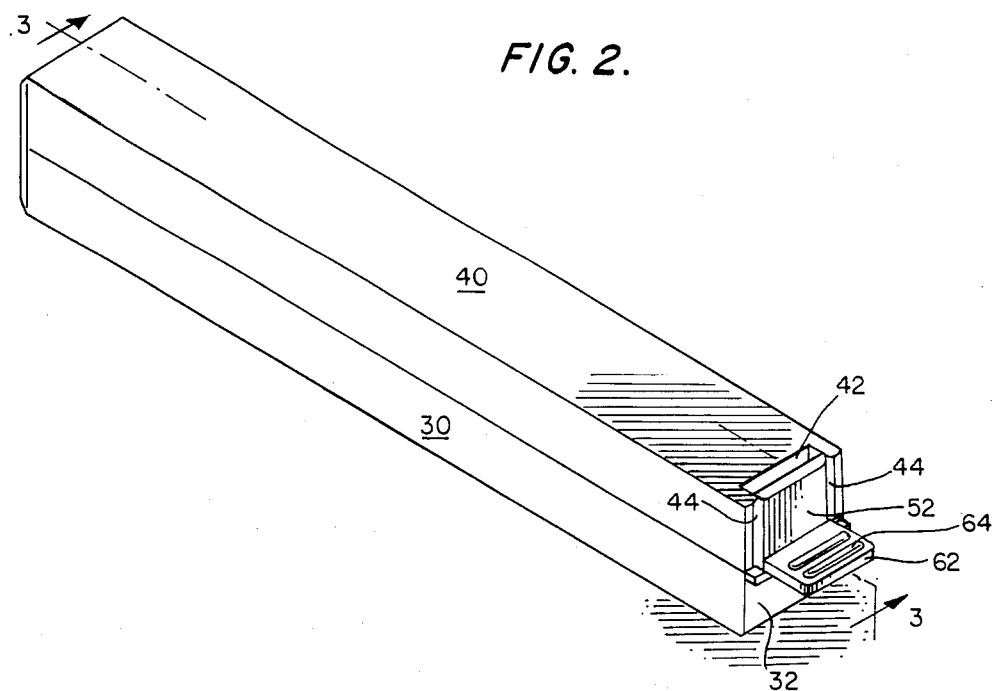
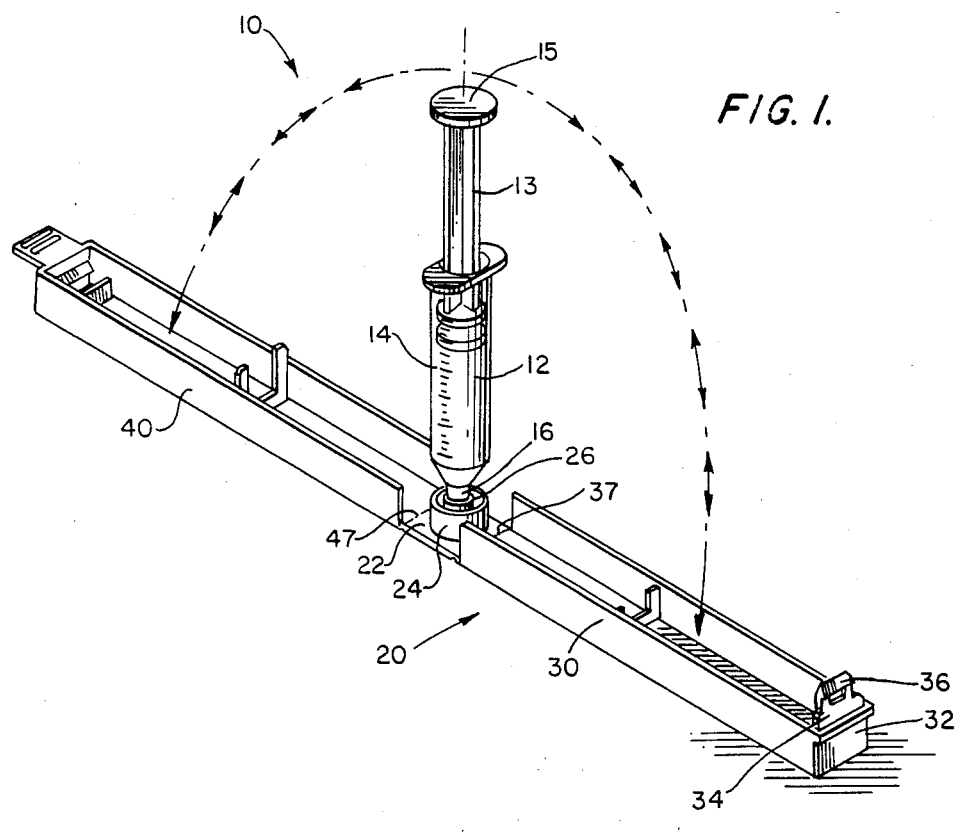
FIG. 2.
FIG. 1.

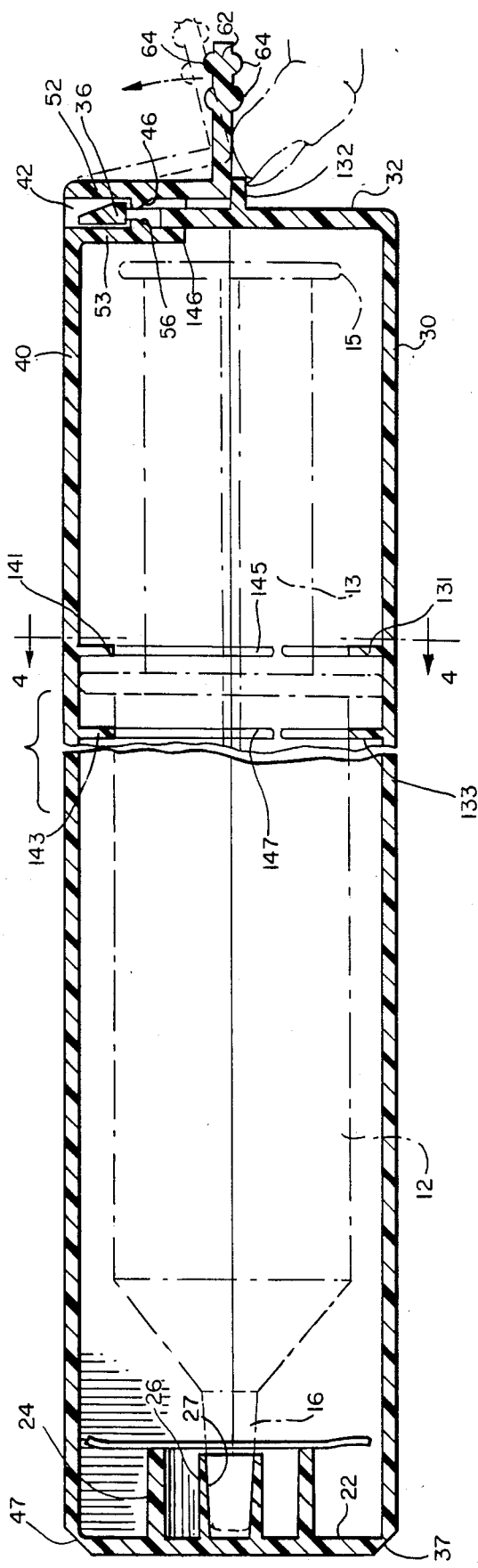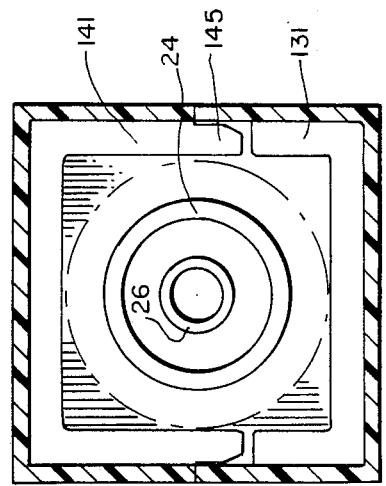

TEMPER-RESISTANT PROTECTIVE CAPPING DEVICE FOR FILLED SYRINGES

BACKGROUND OF THE INVENTION

1. Field of the Invention

This invention relates generally to devices for capping and protecting syringes filled with liquid medication for later use with patients.

2. Description of the Prior Art

A common problem with known protective devices for filled syringes is that they generally are designed for either capping the syringe or for packaging the capped syringe in a tamper-resistant package, but not for both.

For example, U.S. Pat. No. 2,720,969 is a device having a peelable seal which can be used to facilitate the release of the filled syringe from the particular container formation.

U.S. Pat. No. 2,955,705 discloses a transparent container adapted to hold a syringe and needle assembly. However, in this patent, cradle means (see reference numeral 23) are formed on the base section and hold the syringe and needle in position and the cap assembly is then positioned over the base and locked into position. The manner of use of this particular container is entirely different from that of the present invention, and the overall device is not nearly as simple in structure or use as that of the present invention.

U.S. Pat. Nos. 4,043,334 and 4,286,591 are devices that cap or close off the tip of a filled syringe, but do not provide a tamper-resistant enclosure.

SUMMARY OF THE INVENTION

An object of the present invention is to provide a sterile protective container for receiving a filled syringe therewithin and which will provide complete protection therefor until it is desired to use same.

Another object of the present invention is to provide an easily used protective device of one-piece construction wherein the hinge portions of the device are formed as so-called "living hinges" from the material from which the device is made. Also, fastening structure which comprise complementary portions on the respective free ends of the container maintain it in closed protective position until the time of desired use.

A further object of this invention is to provide a one-piece body member having a central female-luer therewith for receiving a filled syringe, a pair of containers affixed on either end of said central body member and connected by hinge means thereto, and complementary clasp means provided at the free ends of the container portions for secure engagement and retention of the device in closed position.

A still further object of the present invention is to provide a protective container device having closure and securement structure associated therewith, which structure can be readily engaged by the fingers of a user, and torn in such a manner as to quickly release the cover from a filled syringe therewithin for immediate use.

Another object of the present invention is to provide a self-contained, sterile syringe cap with tamper evident seal.

The present invention has a number of new and important features. The device comprises a one-piece molded product, including a base section having a portion thereof provided with a luer port, and two side portions which at their furthest ends are provided with locking structure so that when a filled syringe is inserted into the luer taper at the base of the unit, the two side portions can be folded therearound and locked into position to form a tamper-proof container for maintaining a filled syringe in tamper-proof condition.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the protective container device of the present invention with a filled syringe inserted into the central body base section and the protective side portions in the open configuration.

FIG. 2 is a perspective view of the device of FIG. 1 after the side portions have been closed and secured together by the clasp structure at the respective ends thereof.

FIG. 3 is a cross-sectional view taken along line 3—3 of FIG. 2.

FIG. 4 is an end elevational view taken along line 4—4 of FIG. 3.

DESCRIPTION OF THE PREFERRED EMBODIMENT

Referring to FIG. 1 of the drawings, reference numeral 10 indicates in general the device of the present invention. As shown, a filled syringe 12 having indicia 14 inscribed along the side thereof and a plunger portion 13 with head 15 is mounted by the tip 16 in a base section of the protective device.

The base section 22 of the device has a pair of upstanding cylinders 24 and 26 integral therewith. As best seen in FIG. 1, these cylinders 24 and 26 are concentric and the inner cylinder 26 (FIG. 3) provides a female luer taper on the inner surface 27 thereof. This is for reception of the male luer tapered tip 16 of the syringe device 12. Normally, a relatively snug fit is provided for.

On either side of the base section 22 are attached box-like elongated longitudinal containers 30 and 40. Living hinge sections 37 and 47, composed of the same material as the overall device is molded from, allow the box-like containers 30 and 40 to lay flat as depicted in FIG. 1, and then be easily opened and closed as indicated by the double headed arrows in FIG. 1.

The box-like container 30 has a closed end 32 associated therewith with an extension portion 34 extending therefrom. On the outer surface of the end 32 is provided a tapered ridge 36. The purpose of this ridge 36 is to complement and engage with the sawtooth ridge 46 on the end 52 of the other box-like longitudinal cover container 40. The extension portion 34 on the end 32 of the first container 30 is somewhat narrower than the end 52 of the second container 40. Furthermore, indentations or grooves 44 are provided at either side of where the end 52 connects to the outer longitudinal mid-surface of container 40. The grooves 44, together with a slot 42, provide a ready tear portion 152. So that portion 152 can be easily torn open, a traverse tab 62 is provided. The tab 62 preferably also has ribs 64 thereon for increased friction when gripped by the fingers of a user.

As best seen in FIG. 3, an inwardly extending flange 53 parallel to the end portion 52 traverses the inside end of the container 40. Also, when the two cover container portions are closed, as in FIG. 2, the latch structure ridges 36, 46 and 56, due to the tapered leading surfaces thereof, snap together, and then because of the straight backsides of these ridges, lock together.

A lip 132 on the end 32 also abuts the tab 62 when the device is closed. Abutment flanges 131, 133 and 141, 143 provide limit stops for, respectively, a MONOJECT or a B-D syringe. Extensions 145, 147 with the flanges 141, 143 complement the shortened sides of the flanges 131, 133.

FIG. 4 shows in end elevation how the cylinders 24 and 26 are concentrically mounted on the base section 22. The outer cylinder 24 provides a sealing surface for the attachment of a peelable, bacterial barrier BB (see FIG. 3) that is sterilizable by EtO gas or radiation. This material is readily available in the form of surgical draft paper or Dupont's Tyvek ® packaging material.

As can be easily visualized from viewing the drawing figures, the protective cover device of the present invention performs a complete protective container unit for enclosing a filled syringe, and thus will prevent any contamination thereof. However, when it is desired to obtain and use the filled syringe, by merely gripping the extension 62 at the one end of the device, the catch structure 52 can be easily torn off of the end of the device, thus rendering future use of the container impossible, and thus forming a one-time only protective structure.

However, if it is desired that the container be used for more than one application, the slot 42 can be made smaller, or even eliminated completely, as well as the grooves 44 being omitted, and thus the unit would be usable for multi-purpose uses. While such use is envisioned, the primary purpose of the device is for a protective container for filled syringes usable one time only.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A protective capping device for a filled syringe comprising:
   a one-piece structure having a central base portion provided with means for capping the male luer tip of a filled syringe surrounded by a sealing surface covered with a peelable bacterial barrier;
   a pair of longitudinal cover means attached at one end of each by living hinge means which is part of the material of which the device is made to said central base portion;
   one-time only locking means at the respective other ends of each of said pair of cover means for securely holding same together in protective position around said filled syringe when they are closed and which when opened is destroyed to prevent re-use thereof;
   each of said pair of longitudinal cover means including a box-like rectangular structure having at least two sides with one end closed;
   said locking means at the respective other ends of each of the pair of cover structures including a projecting extension from the closed end of one cover structure, said extension having a ridge thereon, and the other cover structure having a pair of separated flanges having a fastening ridge associated therewith for reception of said extension of the other cover therewithin; and
   said pair of flanges on one of said pair of cover structures including a tear-off portion for ease of opening of a closed device.

2. The filled syringe protective device as set forth in claim 1, wherein each rectangular structure has an open end which is associated with the area provided with said hinge means, and said locking means at the respective other ends complement each other.

3. The filled syringe protective device as set forth in claim 1, wherein the device is made of resilient yet flexible plastic material, such as polypropylene, and said hinge area is an area of reduced thickness to provide said living hinge.

4. A protective capping device for a filled syringe comprising:
   a one-piece structure having a central base portion provided with means for capping the male luer tip of a filled syringe surrounded by a sealing surface covered with a peelable bacterial barrier;
   a pair of longitudinal cover means attached at one end of each by living hinge means which is part of the material of which the device is made to said central base portion; and
   one-time only locking means at the respective other ends of each of said pair of cover means for securely holding same together in protective position around said filled syringe when they are closed and which when opened is destroyed to prevent re-use thereof;
   said locking means at the respective other ends of each pair of cover means including complementary structures, one of said structures being a projecting extension with ridge thereon from a closed end of one of said cover means, and the other being a pair of separated flanges having another fastening ridge therewith on the other one of said cover means for reception of said extension of the one cover means therewithin; and
   said pair of flanges on one of said pair of cover means including a tear-off portion for ease of opening of a closed device.

5. A protective cover for a filled syringe comprising: a one-piece body member having a body member with a first cover portion affixed thereto by living hinge means, a second complementary cover portion likewise affixed to said body member by another living hinge portion, and catch means affixed at the respective free ends of each of said cover portions affixed at the respective free ends of each of said cover portions for complementary engagement with each other for tamper-proof locking of the two cover portions together to provide a protective closed container for a filled syringe containing liquids which should be protected from tampering, said means being for one-time use only;
   said catch means at the free ends of each of said covers including an extension on one cover free end having a tapered flange portion therealong for complementary engagement with a recess portion provided in the free end of said other cover;

the recess provided in the free end of said other cover also being provided with an extending sawtooth rib for catching engagement with the tapered flange of said first cover portion;

the recess portion of said other cover having an extension therefrom which extends at right angles to the recess area for ready engagement by the fingers of a user; and said right angle extension being provided with a plurality of finger engaging ribs therealong for maximum frictional engagement by a user, and the bottom of said recess portion being provided with a longitudinal slit which provides for very narrow tear regions at each end of said slit for maximum ease of destruction of the catch means when it is desired to open the protective container.

6. A protective capping device for a filled syringe comprising:

a one-piece plastic structure having a central base portion provided with means for capping the male luer tip of a filled syringe;

a pair of longitudinal cover means attached at one end of each by living hinge means which is part of the plastic material of which the device is made to said central base portion;

one-time only locking means at the respective other ends of each of said pair of cover means for securely holding same together in protective position around said filled syringe when the pair of cover means are closed and which when opened is destroyed to prevent re-use of the device including;

one cover means having a projecting extension from a closed end thereof, said extension having a transverse locking ridge thereon;

the other cover means having a pair of separated flanges with another transverse locking ridge therewith for reception of said extension of said one cover means therewithin so the respective transverse locking ridges will interlock until the locking means is torn apart; and said pair of flanges on one of said pair of cover means including a tear-off portion for ease of opening of a closed device which also self-destructs when the device is opened.

* * * * *